United States Patent
Honda et al.

(10) Patent No.: US 8,759,578 B2
(45) Date of Patent: Jun. 24, 2014

(54) METHOD FOR MANUFACTURING FLUORINE-CONTAINING IMIDE COMPOUND

(75) Inventors: Tsunetoshi Honda, Akita (JP); Noriaki Matsumura, Akita (JP)

(73) Assignees: Mitsubishi Materials Corporation, Tokyo (JP); Mitsubishi Materials Electronic Chemicals Co., Ltd., Akita-shi (JP)

( * ) Notice: Subject to any disclaimer, the term of this patent is extended or adjusted under 35 U.S.C. 154(b) by 0 days.

(21) Appl. No.: 13/699,568

(22) PCT Filed: May 25, 2011

(86) PCT No.: PCT/JP2011/061923
§ 371 (c)(1),
(2), (4) Date: Nov. 21, 2012

(87) PCT Pub. No.: WO2011/148958
PCT Pub. Date: Dec. 1, 2011

(65) Prior Publication Data
US 2013/0066110 A1    Mar. 14, 2013

(30) Foreign Application Priority Data

May 26, 2010 (JP) ................................. 2010-120657

(51) Int. Cl.
C07C 303/00 (2006.01)
C07C 307/00 (2006.01)
C07C 309/00 (2006.01)
C07C 311/00 (2006.01)
C07C 303/38 (2006.01)

(52) U.S. Cl.
CPC .................................. *C07C 303/38* (2013.01)
USPC ......................................................... 564/82

(58) Field of Classification Search
USPC ......................................................... 564/82
See application file for complete search history.

(56) References Cited

FOREIGN PATENT DOCUMENTS

| CN | 1640895 A | 7/2005 |
|----|-----------|--------|
| FR | 2818994 A1 | 7/2002 |
| JP | 08-081436 A | 3/1996 |
| JP | 2001-288193 A | 10/2001 |
| JP | 2004-269491 A | 9/2004 |
| JP | 2005-200359 A | 7/2005 |
| JP | 2008-222660 A | 9/2008 |

OTHER PUBLICATIONS

Han et al. (Efficient Preparation of (Fluorosulfonyl)(pentafluoroethanesulfonyl)imide and Its Alkali Salts, Chem. Lett. 2010, 39, pp. 472-474, Published on the web Mar. 31, 2010).*
R. Appel et al., "Synthesis of Imidodisulfuric acid fluoride HN(SO$_2$F)$_2$," Chem. Ber., 95, 1962, pp. 246-248 and English translation thereof.
H-B Han et al., "Efficient Preparation of (Fluorosulfonyl)(pentafluoroethanesulfonyl)imide and Its Alkali Salts," Chemistry Letters, vol. 39, No. 5, p. 472-474 published on the web: Mar. 31, 2010 and p. 1-6.
International Search Report dated Jun. 28, 2011, issued for PCT/JP2011/061923.
Office Action dated Jul. 1, 2013, issued for the Chinese patent application No. 201180025426.7 and English translation of the Search Report.
Notice of Reasons for Rejection issued in corresponding Japanese Patent Application No. JP2012-517287, dated Jan. 7, 2014.
H. W. Roesky et al. "Preparation of N-trifluoromethanesulphonyl-sulphonylfluoride amide and some reactions.," Inorg. Nucl. Chem. Letters vol. 7, pp. 171-175 (1971).

* cited by examiner

*Primary Examiner* — Brandon Fetterolf
*Assistant Examiner* — Blaine G Doletski
(74) *Attorney, Agent, or Firm* — Edwards Wildman Palmer LLP; James E. Armstrong, IV

(57) ABSTRACT

With this method for manufacturing fluorine-containing imide compounds, a method for manufacturing a fluorine-containing imide compound ((Rf$^1$SO$_2$)(Rf$^2$SO$_2$)NH) is selected which includes reaction of a fluorine-containing sulfonic acid (Rf$^1$SO$_3$H) and a fluorine-containing sulfonamide (Rf$^2$SO$_2$NH) in the presence of thionyl chloride. Wherein, Rf$^1$ and Rf$^2$ are fluorine, or straight-chain or branched perfluoroalkyl groups with a carbon number of 1-4.

10 Claims, No Drawings

METHOD FOR MANUFACTURING FLUORINE-CONTAINING IMIDE COMPOUND

TECHNICAL FIELD

The present invention relates to an improved method for manufacturing fluorine-containing imide compounds.

Priority is claimed on Japanese Patent Application No. 2010-120657, filed May 26, 2010, the content of which is incorporated herein by reference.

BACKGROUND ART

Fluorinated imide compounds (fluorine-containing imide compounds) are known to be useful substances as anionic sources of ion conducting material or ionic liquid. Ionic liquid is particularly useful as an electrolyte, reaction solvent, catalyst or the like in batteries and capacitors. This ionic liquid is generally known to be obtained by the base exchange of, for example, salt of fluorine-containing sulfonyl imide acid which is a fluorinated imide compound, and halide salt of quaternary amines such as imidazolium bromide salt.

As methods of manufacture of fluorine-containing imide compounds, the methods described in Non-Patent Document 1 and Patent Documents 1-3 are known. Specifically, Non-Patent Document 1 discloses a method wherein, as shown in the following formula (A), fluorosulfonic acid ($FSO_3H$) and urea (($NH_2)_2CO$) are reacted, and the generated bis(fluorosulfonyl)imide ($FSO_2)_2NH$ and excess fluorosulfonic acid are recovered by reduced-pressure distillation under heating.

[Chemical formula 1]

$$3FSO_3H + CO(NH_2)_2 \rightarrow (FSO_2)_2NH + NH_4HSO_4 + HF + CO_2 \quad (A)$$

Patent Document 1 discloses a method wherein perfluoroalkylsulfonamide ($RfSO_2NH_2$; Rf is a perfluoroalkyl group) is converted to salt of Na, K, Li or the like, and this is reacted with disulfuryl fluoride (($FSO_2)_2O$) or sulfuryl fluoride halide ($SO_2FX$; X is a halogen atom).

Patent Document 2 discloses a method wherein, as shown in the following formula (B); perfluoroalkyl sulfonamide ($Rf^aSO_2NH_2$), perfluoroalkyl sulfonyl halide ($Rf^bSO_2X$), and a fluorine compound (MF) such as potassium fluoride are reacted with an organic solvent such as acetonitrile to produce perfluoroalkyl sulfonyl imide salt (($Rf^aSO_2)(Rf^bSO_2)N.M$).

[Chemical formula 2]

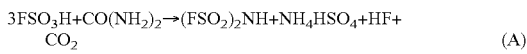

$$Rf^aSO_2NH_2 + Rf^bSO_2X + 4MF \rightarrow (Rf^aSO_2)(Rf^bSO_2)N.M + 2MFHF + MX \quad (B)$$

In said formula (B), $Rf^a$ and $Rf^b$ indicate perfluoroalkyl groups or the like, M indicates alkali metal or the like, and X indicates fluorine or chlorine, respectively.

Patent Document 3 discloses a method wherein, as shown in the following formula (C), perfluoroalkyl sulfonamide and perfluoroalkyl sulfonyl halide are reacted in the presence of a tertiary amine or heterocyclic amine ($NR^1R^2R^3$) to produce perfluoroalkyl sulfonyl imide salt (($Rf^cSO_2)(Rf^dSO_2)N.R^1R^2R^3NH$).

[Chemical formula 3]

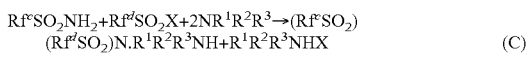

$$Rf^cSO_2NH_2 + Rf^dSO_2X + 2NR^1R^2R^3 \rightarrow (Rf^cSO_2)(Rf^dSO_2)N.R^1R^2R^3NH + R^1R^2R^3NHX \quad (C)$$

In said formula (C), $Rf^c$ and $Rf^d$ indicate perfluoroalkyl groups or the like, and $R^1$ to $R^3$ indicate alkyl groups or the like, respectively.

PRIOR ART REFERENCES

Patent Documents

Patent Document 1: Japanese Unexamined Patent Application, First Publication No. 2005-200359
Patent Document 2: Japanese Unexamined Patent Application, First Publication No. 2001-288193
Patent Document 3: Japanese Unexamined Patent Application, First Publication No. H8-81436

Non-Patent Documents

Non-Patent Document 1: Chem. Ber., 95, 246-8, 1962, Appel, Eisenhauer.

DISCLOSURE OF INVENTION

Problems that the Invention is to Solve

However, with the method described in Non-Patent Document 1, there is the problem that the reaction of urea and perfluorosulfonic acid is a reaction accompanied by production of carbon dioxide gas and significant heat generation, and results in a runaway reaction. Consequently, the method described in Non-Patent Document 1 is a method in which the reaction is difficult to control, and which is difficult to industrially implement.

With the method described in Patent Document 1, there is the problem that the disulfuryl fluoride which is a raw material is difficult to obtain, and is extremely difficult to handle due to its violent reaction with water. In addition, there is the problem that a particular kind of apparatus such as an autoclave is required for reaction, because sulfuryl fluoride is a gas at room temperature.

With the methods described in Patent Documents 2 and 3, there is the problem that when perfluoroalkyl sulfonamide and perfluoroalkyl sulfonyl halide are reacted to generate perfluoroalkyl sulfonyl imide salt, it is necessary to add large amounts of expensive alkali metal fluoride or tertiary amine as an additive for imidization reaction.

Furthermore, when the carbon number of Rf is 1 or 2, the boiling point of the perfluoroalkyl sulfonyl halide which is the raw material is low, with the result that a particular kind of reaction apparatus such as an autoclave is required for synthesis.

As a previously known method of synthesis of perfluoroalkyl sulfonimide using perfluoroalkyl sulfonamide, there is the reaction of perfluoroalkyl sulfonamide and perfluoroalkyl sulfonic anhydride, or of perfluoroalkyl sulfonamide and perfluoroalkyl sulfonyl halide. However, there is no known method for synthesizing fluorine-containing sulfonimide from fluorine-containing sulfonamide and fluorine-containing sulfonic acid, because the reactivity of fluorine-containing sulfonic acid is low.

The present invention was made in light of the foregoing problems, and its object is to provide a method for manufacturing fluorine-containing imide compounds with a high degree of safety and productivity using inexpensive raw materials.

Means for Solving the Problems

In order to solve the foregoing problems, the present inventors discovered as a result of diligent research that it is possible to cause the reaction of fluorine-containing sulfonamide and fluorine-containing sulfonic acid in the presence of thionyl chloride (SOCl$_2$), thereby perfecting the present invention That is, the present invention adopts the following configuration.

[1] A method for manufacturing a fluorine-containing imide compound shown in the following formula (1), which causes reaction of a fluorine-containing sulfonic acid shown in the following formula (2) and a fluorine-containing sulfonamide shown in the following formula (3) in the presence of thionyl chloride.

$(Rf^1SO_2)(Rf^2SO_2)NH$     (1)

$Rf^1SO_3H$     (2)

$Rf^2SO_2NH_2$     (3)

However, in said formulas (1)-(3), $Rf^1$ and $Rf^2$ are fluorine, or straight-chain or branched perfluoroalkyl groups with a carbon number of 1-4.

[2] The method for manufacturing a fluorine-containing compound according to item [1] above, wherein: the fluorine-containing imide compound shown in said formula (1) is a trifluoro-N-(fluorosulfonyl)methanesulfonyl amide shown in the following formula (4);
the fluorine-containing sulfonic acid shown in said formula (2) is a fluorosulfonic acid shown in the following formula (5); and
the fluorine-containing sulfonamide shown in said formula (3) is a trifluoromethyl sulfonamide shown in the following formula (6).

$(FSO_2)(CF_3SO_2)NH$     (4)

$FSO_3H$     (5)

$CF_3SO_2NH_2$     (6)

[3] The method for manufacturing a fluorine-containing imide compound according to item [1] or item [2] above, including a step in which said thionyl chloride is dissolved in said fluorine-containing sulfonic acid to produce a solution, and a step in which reaction is caused by heating said solution, and by adding said fluorine-containing sulfonamide thereto.

[4] The method for manufacturing a fluorine-containing imide compound according to item [1] or item [2] above, including a step in which said fluorine-containing sulfonamide is dissolved in said fluorine-containing sulfonic acid to produce a solution, and a step in which reaction is caused by heating said solution, and by instilling said thionyl chloride therein.

[5] The method for manufacturing a fluorine-containing imide compound according to item [1] or item [2] above, including a step in which said fluorine-containing sulfonic acid, said fluorine-containing sulfonamide, and said thionyl chloride are mixed to produce a liquid mixture, and a step in which reaction is caused by heating said liquid mixture.

[6] The method for manufacturing a fluorine-containing imide compound according to any one of items [1] to [5] above, wherein the reaction temperature is in a range of 50-140° C.

Effects of the Invention

According to the method for manufacturing fluorine-containing imide compounds of the present invention, by causing reaction of a fluorine-containing sulfonic acid and a fluorine-containing sulfonamide in the presence of thionyl chloride, it is possible to synthesize a fluorine-containing imide compound from a fluorine-containing sulfonic acid and a fluorine-containing sulfonamide. Accordingly, it is possible to offer a high-yield method for manufacturing fluorine-containing imide compounds using raw materials that are easy to obtain and easy to handle in industrial terms.

BEST MODE FOR CARRYING OUT THE INVENTION

The method for manufacturing fluorine-containing imide compounds of the present invention is described below in detail.

The method for manufacturing fluorine-containing imide compounds of the present embodiment is the method for manufacturing fluorine-containing imide compounds shown in the following formula (7), wherein a fluorine-containing sulfonic acid shown in the following formula (8) and a fluorine-containing sulfonamide shown in the following formula (9) are reacted in the presence of thionyl chloride (SOCl$_2$).

$(Rf^1SO_2)(Rf^2SO_2)NH$     (7)

$Rf^1SO_3H$     (8)

$Rf^2SO_2NH_2$     (9)

However, in said formulas (7)-(9), $Rf^1$ and $Rf^2$ are fluorine, or straight-chain or branched perfluoroalkyl groups with a carbon number of 1-4.

It is inferred that the reaction mechanism of the present embodiment is that a fluorine-containing imide compound shown in said formula (7), hydrogen chloride (HCl), and sulfur dioxide (SO$_2$) are produced by reacting a fluorine-containing sulfonic acid shown in said formula (8) and a fluorine-containing sulfonamide shown in said formula (9) in the presence of thionyl chloride (SOCl$_2$) by the chemical reaction shown in the following formula (10).

As an advantage of the present embodiment, the hydrogen chloride and the sulfur dioxide which are by-products are gas, and they consequently do not remain in the reaction system.

[Chemical formula 4]

$Rf^1SO_3H + Rf^2SO_2NH_2 + SOCl_2 \rightarrow (Rf^1SO_2)(Rf^2SO_2)NH + 2HCl + SO_2$     (10)

However, in said formulas (10), $Rf^1$ and $Rf^2$ are fluorine, or straight-chain or branched perfluoroalkyl groups with a carbon number of 1-4.

(Fluorine-Containing Sulfonic Acid)

In the method for manufacturing fluorine-containing imide compounds of the present embodiment, as the fluorine-containing sulfonic acid represented by said formulas (8) which is one of the raw materials, one may cite fluorosulfonic acid (FSO$_3$H), as well as trifluoromethyl sulfonic acid (CF$_3$SO$_3$H), pentafluorethyl sulfonic acid (C$_2$F$_5$SO$_3$H), heptafluoropropyl sulfonic acid (C$_3$F$_7$SO$_3$H), and nonafluorobutyl sulfonic acid (C$_4$F$_9$SO$_3$H) which are a perfluoroalkyl sulfonic acid. Of these fluorine-containing sulfonic acids in the method for manufacturing fluorine-containing imide compounds of the present embodiment, use of fluorosulfonic acid is preferable, because it enables manufacture of pentafluoro-N-(fluorosulfonyl)alkanesulfonyl amide, which has conventionally been difficult to do.

(Fluorine-Containing Sulfonamide)

As the fluorine-containing sulfonamide represented by said formula (9) which is another raw material, one may cite fluorosulfonamide (FSO$_2$NH$_2$), as well as trifluoromethyl sulfonamide (CF$_3$SO$_2$NH$_2$), pentafluorethyl sulfonamide ($C_2F_5SO_2NH_2$), heptafluoropropyl sulfonamide ($C_3F_7SO_2NH_2$), and nonafluorobutyl sulfonamide ($C_4F_9SO_2NH_2$), which are a perfluoroalkyl sulfonamide. Among these fluorine-containing sulfonamides in the method of manufacture the fluorine-containing imide compounds of the present embodiment, use of trifluoromethyl sulfonamide, pentafluoroethyl sulfonamide, heptafluoropropyl sulfonamide, nonafluorobutyl sulfonamide and the like is preferable from the standpoint of easy obtainment of raw material, and use of trifluoromethyl sulfonamide is most preferable from the standpoint of particularly easy obtainment of raw material.

(Fluorine-Containing Imides)

The method for manufacturing fluorine-containing imide compounds of the present embodiment is particularly effective in synthesis of asymmetric fluorine-containing imide compounds of which either $Rf^1$ or $Rf^2$ is fluorine, and which have conventionally been difficult to manufacture.

With respect to the fluorine-containing imide compounds represented by said formula (7), as cases where $Rf^1$ and $Rf^2$ are identical (have a symmetric structure), one may cite perfluoroalkyl sulfonimides such as bis(fluorosulfonyl)imide [$(FSO_2)_2NH$], bis(trifluoromethanesulfonyl)imide [$(CF_3SO_2)_2NH$], bis(pentafluoroethanesulfonyl)imide [$(C_2F_5SO_2)_2NH$], bis(pentafluoropropanesulfonyl)imide [$(C_3F_7SO_2)_2NH$], and bis(nonafluorobutanesulfonyl)imide [$(C_4F_9SO_2)_2NH$]. With respect to $Rf^1$ and $Rf^2$ of the present embodiment, in the case where the carbon number is 3 or 4, branched structural isomers are included in addition to the straight-chain form (the same applies hereinafter when the carbon number is 3 or 4).

As fluorine-containing imide compounds where $Rf^1$ and $Rf^2$ are different (have an asymmetric structure), one may cite trifluoro-N-(fluorosulfonyl)methane sulfonylamide [$(FSO_2)(CF_3SO_2)NH$], pentafluoro-N-(fluorosulfonyl)ethane sulfonylamide [$(FSO_2)(C_2F_5SO_2)NH$], heptafluoro-N-(fluorosulfonyl)propane sulfonylamide [$(FSO_2)(C_3F_7SO_2)NH$], nonafluoro-N-(fluorosulfonyl)butane sulfonylamide [$(FSO_2)(C_4F_9SO_2)NH$], pentafluoro-N-[(trifluoromethane)sulfonyl]ethane sulfonylamide [$(CF_3SO_2)(C_2F_5SO_2)NH$], heptafluoro-N-[(trifluoromethane)sulfonyl]propane sulfonylamide [$(CF_3SO_2)(C_3F_7SO_2)NH$], nonafluoro-N-[(trifluoromethane)sulfonyl]butane sulfonylamide [$(CF_3SO_2)(C_4F_9SO_2)NH$], heptafluoro-N-[(pentafluoroethane)sulfonyl]propane sulfonylamide [$(C_2F_5SO_2)(C_3F_7SO_2)NH$], nonafluoro-N-[(pentafluoroethane)sulfonyl]butane sulfonylamide [$(C_2F_5SO_2)(C_4F_9SO_2)NH$], nonafluoro-N-[(heptafluoropropane)sulfonyl]butane sulfonylamide [$(C_3F_7SO_2)(C_4F_9SO_2)NH$], and the like.

In the case where an asymmetric fluorine-containing imide compound in which either $Rf^1$ or $Rf^2$ is fluorine is manufactured by a conventional method for manufacturing fluorine-containing imide compounds, manufacture is difficult compared to the case where other fluorine-containing imide compounds are manufactured. The method for manufacturing fluorine-containing imide compounds of the present embodiment is effective in synthesis of asymmetric fluorine-containing imide compounds in which either $Rf^1$ or $Rf^2$ is fluorine.

With the method for manufacturing fluorine-containing imide compounds of the present embodiment, synthesis of trifluoro-N-(fluorosulfonyl)methane sulfonylamide among said asymmetric fluorine-containing imide compounds is more preferable from the standpoint of easy obtainment of raw material.

With the method for manufacturing fluorine-containing imide compounds of the present embodiment, it is particularly preferable to respectively use fluorosulfonic acid ($FSO_3H$) as the fluorine-containing sulfonic acid shown in said formula (8), and trifluoromethyl sulfonamide ($CF_3SO_2NH_2$) as the fluorine-containing sulfonamide shown in said formula (9), and to apply them when synthesizing trifluoro-N-(fluorosulfonyl)methane sulfonamide [$(FSO_2)(CF_3SO_2)NH$], which is an asymmetric fluorine-containing imide compound in which $Rf^1$ and $Rf^2$ are different, as the fluorine-containing imide compound represented by said formula (7).

The first procedure of the method for manufacturing fluorine-containing imide compounds of the present embodiment is a method for manufacturing fluorine-containing imide compounds including a step (solution production step) in which thionyl chloride is dissolved in fluorine-containing sulfonic acid to produce a solution, and a step (addition and reaction step) in which reaction is caused by heating this solution, and adding fluorine-containing sulfonamide thereto. A specific description of each step is given below.

(Solution Production Step)

First, fluorine-containing sulfonic acid and thionyl chloride are injected into a reaction vessel without reacting, and the thionyl chloride dissolves in the fluorine-containing sulfonic acid to produce a solution.

Now, the amount of fluorine-containing sulfonic acid is preferably 1-20-fold and more preferably 1-8-fold in terms of mol ratio relative to the fluorine-containing sulfonamide that is added. It is undesirable when the fluorine-containing sulfonic acid is less than 1-fold in mol ratio relative to the fluorine-containing sulfonamide that is added, because the fluorine-containing sulfonic acid that is required for reaction is insufficient, lowering the yield of fluorine-containing imide compound. On the other hand, it is economically wasteful when the amount of fluorine-containing sulfonic acid exceeds 20-fold in mol ratio relative to the fluorine-containing sulfonamide that is added.

The amount of thionyl chloride is preferably 1-10-fold and more preferably 1-5-fold in terms of mol ratio relative to the fluorine-containing sulfonamide that is added. It is undesirable when the thionyl chloride is less than 1-fold in mol ratio relative to the fluorine-containing sulfonamide that is added, because the thionyl chloride that is required for reaction is insufficient, lowering the yield of fluorine-containing imide compound. On the other hand, it is economically wasteful when the amount of thionyl chloride exceeds 10-fold in mol ratio relative to the fluorine-containing sulfonamide that is added.

In the present embodiment, it is thought that reactivity is enhanced by causing reaction of fluorine-containing sulfonic acid and fluorine-containing sulfonamide in the presence of thionyl chloride.

(Addition and Reaction Step)

In the addition and reaction step, first, said solution that was injected into the reaction vessel is heated. Next, fluorine-containing sulfonamide is added to said reaction vessel that has been heated. In this manner, fluorine-containing sulfonic acid and fluorine-containing sulfonamide react in the presence of thionyl chloride.

Now, the reaction temperature inside the reaction vessel during addition of the fluorine-containing sulfonamide is preferably in a range of 50-140° C., and more preferably in a range of 60-120° C. It is undesirable when the reaction temperature is less than 50° C., because progression of the reaction is slowed. On the other hand, it is undesirable when 140° C. is exceeded, because the thionyl chloride volatilizes. Accordingly, the temperature of the pre-heated solution of fluorine-containing sulfonic acid and thionyl chloride is preferably heated to, for example, 60-120° C.

The second procedure of the method for manufacturing fluorine-containing imide compounds of the present embodiment is a method for manufacturing fluorine-containing imide compounds including a step (solution production step) in which fluorine-containing sulfonamide is dissolved in fluorine-containing sulfonic acid to produce a solution, and a step (instillation and reaction step) in which reaction is caused by heating this solution, and instilling thionyl chloride therein.

Now, relative to the above-described first procedure, the second procedure transposes the thionyl chloride that is dissolved in the fluorine-containing sulfonic acid, and the added fluorine-containing sulfonamide, but conditions pertaining to the respective input amounts of the raw materials and the reaction temperature inside the reaction vessel are identical to those of the first procedure.

Furthermore, the third procedure of the present embodiment is a method for manufacturing fluorine-containing imide compounds including a step (liquid mixture production step) in which fluorine-containing sulfonic acid, fluorine-containing sulfonamide, and thionyl chloride are mixed to produce a liquid mixture, and a step (heating and reaction step) in which this liquid mixture is reacted by heating.

Now, relative to the above-described first and second procedures, the third procedure conducts heating after the thionyl chloride and fluorine-containing sulfonamide have been dissolved in advance in the fluorine-containing sulfonic acid, but conditions pertaining to the respective input amounts of the raw materials and the reaction temperature inside the reaction vessel are identical to those of the first procedure.

As described above, according to the method for manufacturing fluorine-containing imide compounds of the present embodiment, fluorine-containing sulfonic acid and fluorine-containing sulfonamide are reacted in the presence of thionyl chloride, thereby enabling synthesis of a fluorine-containing imide compound from fluorine-containing sulfonic acid and fluorine-containing sulfonamide. Accordingly, it is possible to offer a method for manufacturing fluorine-containing imide compounds in high yield using raw materials which are easy to obtain and easy to handle in industrial terms.

According to the method for manufacturing fluorine-containing imide compounds of the present embodiment, fluorine-containing sulfonic acid and fluorine-containing sulfonamide are combined and reacted, whereby fluorine-containing sulfonimide of symmetric structure and asymmetric structure can be easily manufactured.

It is also thought that according to the method for manufacturing fluorine-containing imide compounds of the present embodiment, it is possible to enhance reactivity by adding thionyl chloride to the reaction system. By this means, it is possible to offer a previously unknown method of synthesizing fluorine-containing imide compounds from a fluorine-containing sulfonamide and a fluorine-containing sulfonic acid.

Moreover, according to the method for manufacturing fluorine-containing imide compounds of the present embodiment, as the fluorine-containing sulfonic acid that is one of the raw materials has a high boiling point, fluorine-containing imide compounds can be conveniently manufactured without using a particular kind of apparatus such as an autoclave.

In addition, according to the method for manufacturing fluorine-containing imide compounds of the present embodiment, fluorine-containing imide compounds used in battery electrolyte or the like can be synthesized from sulfonamide and sulfonic acid.

EXAMPLES

The effects of the present invention are described in further detail below by means of examples. The present invention is not limited in any way by the examples.

Example 1

A 100 ml glass reaction vessel provided with an agitator and a thermometer was charged with 30 g of trifluoromethyl sulfonamide, 46 g of thionyl chloride, and 88 g of fluorosulfonic acid, and a reaction was conducted for 12 hours at 120° C. During the reaction, generation of hydrogen chloride gas and sulfur dioxide gas was confirmed.

The reaction solution was instilled into water, and analysis was conducted by $^{19}$F-NMR. Peaks of trifluoro-N-(fluorosulfonyl)methane sulfonylamide were respectively confirmed at 56.7 ppm and −78.3 ppm.

The yield of trifluoro-N-(fluorosulfonyl)methane sulfonylamide under the trifluoromethyl sulfonamide standard was 70% according to the internal standard addition method.

Example 2

A 100 ml glass reaction vessel provided with an agitator and a thermometer was charged with 50 g of fluorosulfonic acid, and 15 g of trifluoromethyl sulfonamide, and heated to 120° C. A reaction was conducted for 12 hours at 120° C., and 24 g of thionyl chloride was instilled into the heated reaction solution over a 2-hour period. During instillation, generation of hydrogen chloride gas and sulfur dioxide gas was confirmed.

After instillation, reaction was conducted for two hours at 120° C. After reaction, the reaction solution was instilled into water, and analysis was conducted by $^{19}$F-NMR. Peaks of trifluoro-N-(fluorosulfonyl)methane sulfonylamide were respectively confirmed at 56.7 ppm and −78.3 ppm.

The yield of trifluoro-N-(fluorosulfonyl)methane sulfonylamide under the trifluoromethyl sulfonamide standard was 81% according to the internal standard addition method.

Comparative Example 1

A 100 ml glass reaction vessel provided with an agitator and a thermometer identical to the apparatus of example 1 was charged with 45 g of fluorosulfonic acid, and heated to 80° C. 22 g of trifluoromethyl sulfonamide were added, and reaction was conducted for 130 hours also at 80° C.

The reaction solution was instilled into water, and analysis was conducted by $^{19}$F-NMR. No peaks of trifluoro-N-(fluorosulfonyl)methane sulfonylamide were detected.

INDUSTRIAL APPLICABILITY

With the method for manufacturing fluorine-containing imide compounds illustrated in the present embodiment, manufacture of fluorine-containing imide compounds can be conducted using fluorine-containing sulfonic acid, fluorine-containing sulfonamide, and thionyl chloride, which are easy to obtain in industrial terms, and the manufactured fluorine-containing imide compounds can be employed in an industrially useful manner as anionic sources of ion conducting materials or ionic liquids.

The invention claimed is:

1. A method for manufacturing a trifluoro-N-(fluorosulfonyl)methanesulfonyl imide shown in the following formula (4), which is caused from a reaction of a fluorosulfonic acid shown in the following formula (5) and a trifluoromethyl sulfonamide shown in the following formula (6) in the presence of thionyl chloride:

$$(FSO_2)(CF_3SO_2)NH \quad (4)$$

$$FSO_3H \quad (5)$$

$$CF_3SO_2NH_2 \quad (6).$$

2. The method for manufacturing the trifluoro-N-(fluorosulfonyl)methanesulfonyl imide according to claim 1, comprising:
 a step in which said thionyl chloride is dissolved in said fluorosulfonic acid to produce a solution, and
 a step in which a reaction is caused by heating said solution, and by adding said trifluoromethyl sulfonamide thereto.

3. The method for manufacturing the trifluoro-N-(fluorosulfonyl)methanesulfonyl imide according to claim 1, comprising:
 a step in which said trifluoromethyl sulfonamide is dissolved in said fluorosulfonic acid to produce a solution, and
 a step in which a reaction is caused by heating said solution, and by instilling said thionyl chloride therein.

4. The method for manufacturing the trifluoro-N-(fluorosulfonyl)methanesulfonyl imide according to claim 1, comprising:
 a step in which said fluorosulfonic acid, said trifluoromethyl sulfonamide, and said thionyl chloride are mixed to produce a liquid mixture, and
 a step in which a reaction is caused by heating said liquid mixture.

5. The method for manufacturing the trifluoro-N-(fluorosulfonyl)methanesulfonyl imide according to claim 1, wherein the reaction temperature is in a range of 50-140° C.

6. The method for manufacturing the trifluoro-N-(fluorosulfonyl)methanesulfonyl imide according to claim 1, wherein the amount of the fluorosulfonic acid is 1 to 20 fold in terms of molar ratio relative to the trifluoromethyl sulfonamide that is added.

7. The method for manufacturing the trifluoro-N-(fluorosulfonyl)methanesulfonyl imide according to claim 1, wherein the amount of the fluorosulfonic acid is 1 to 8 fold in terms of molar ratio relative to the trifluoromethyl sulfonamide that is added.

8. The method for manufacturing the trifluoro-N-(fluorosulfonyl)methanesulfonyl imide according to claim 1, wherein the amount of the thionyl chloride is 1 to 10 fold in terms of molar ratio relative to the trifluoromethyl sulfonamide that is added.

9. The method for manufacturing the trifluoro-N-(fluorosulfonyl)methanesulfonyl imide according to claim 1, wherein the amount of the thionyl chloride is 1 to 5 fold in terms of molar ratio relative to the trifluoromethyl sulfonamide that is added.

10. The method for manufacturing the trifluoro-N-(fluorosulfonyl)methanesulfonyl imide according to claim 1, wherein the reaction temperature is in a range of 60-120° C.

\* \* \* \* \*